_United States Patent_ [19]

Böshagen et al.

[11] Patent Number: 4,806,551
[45] Date of Patent: Feb. 21, 1989

[54] N-DIHYDROINDOLYLETHYL-SULPHONA-MIDES

[75] Inventors: Horst Böshagen, Haan; Ulrich Rosentreter, Wuppertal; Folker Lieb, Leverkusen; Hermann Oediger, Cologne; Volker-Bernd Fiedler, Leverkusen; Elisabeth Perzborn; Friedel Seuter, both of Wuppertal, all of Fed. Rep. of Germany

[73] Assignee: Bayer Aktiengesellschaft, Leverkusen, Fed. Rep. of Germany

[21] Appl. No.: 39,395

[22] Filed: Apr. 16, 1987

[30] Foreign Application Priority Data

Apr. 23, 1986 [DE] Fed. Rep. of Germany ....... 3613623

[51] Int. Cl.$^4$ ................. C07D 209/34; C07D 209/16; C07D 209/14; A61K 31/40
[52] U.S. Cl. ..................... 514/415; 548/486; 548/507; 514/418
[58] Field of Search ............... 548/507, 486; 514/415, 514/418

[56] References Cited

U.S. PATENT DOCUMENTS 3,833,608  9/1974  Rooney ............................ 548/407
4,636,521  1/1987  Coates ............................. 548/407

_Primary Examiner_—Mark L. Berch
_Attorney, Agent, or Firm_—Sprung Horn Kramer & Woods

[57] ABSTRACT

New N-dihydroindolylethyl-sulphonamides are prepared from the corresponding N-indolylethyl-sulphonamides by oxidation or hydrogenation and are useful as active compounds in medicaments. These compounds exhibit a platelet aggregation-inhibiting and thromboxan A$_2$-antagonistic action.

The N-dihydroindolylethyl-sulphonamides have the formula

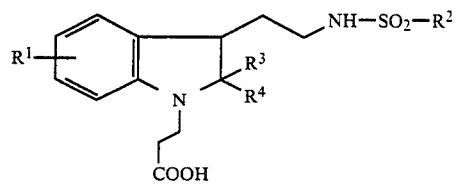

in which
  $R^1$ represents hydrogen, halogen, trifluoromethyl, carboxyl or alkoxycarbonyl, or represents a group of the formula —$S(O)_mR^5$,
wherein
  $R^5$ denotes alkyl or aryl and
  m denotes one of the numbers 0, 1 or 2, or
  $R^1$ represents a group of the formula

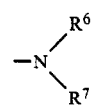

or
  $R^1$ represents a group of the formula —$OR^8$, or
  $R^1$ represents optionally substituted alkyl, alkenyl or cycloalkyl,
  $R^2$ represents aryl, which is optionally substituted by up to 5 substituents,
  $R^3$ represents hydrogen or alkyl and
  $R^4$ represents hydrogen, or
  $R^3$ and $R^4$ together bond a carbonyl-oxygen.

7 Claims, No Drawings

N-DIHYDROINDOLYLETHYL-SULPHONAMIDES

The invention relates to new N-dihydroindolyl-ethyl-sulphonamides, processes for their preparation and their use in medicaments.

New N-dihydroindolylethyl-sulphonamides of the general formula (I)

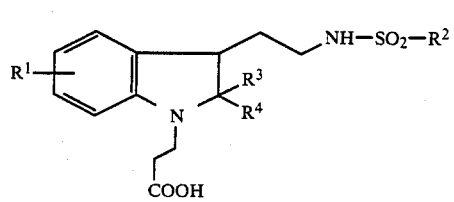

in which
$R^1$ represents hydrogen, halogen, trifluoromethyl, carboxyl or alkoxycarbonyl, or represents a group of the formula $—S(O)_mR^5$,
wherein
$R^5$ denotes alkyl or aryl and
m denotes one of the numbers 0, 1 or 2, or
$R^1$ represents a group of the formula

wherein
$R^6$ and $R^7$ are identical or different and denote hydrogen, alkyl, aryl, aralkyl or acyl, or
$R^1$ represents a group of the formula $—OR^8$,
wherein
$R^8$ denotes hydrogen, alkyl, aryl, aralkyl, alkylsulphonyl, arylsulphonyl, aralkylsulphonyl or trifluoromethyl, or
$R^1$ represents alkyl, alkenyl or cycloalkyl, optionally substituted by carboxyl, alkoxycarbonyl, halogen, hydroxyl, alkoxy, alkylthio or cyano,
$R^2$ represents aryl, which is optionally substituted by up to 5 substituents selected from the group consisting of halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy and benzylthio or by a group of the formula

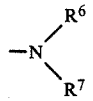

in which
$R^6$ and $R^7$ have the abovementioned meaning,
$R^3$ represents hydrogen or alkyl and
$R^4$ represents hydrogen, or
$R^3$ and $R^4$ together bond a carbonyl oxygen,
and salts thereof, have been found.

The substances according to the invention have several asymmetric carbon atoms and can therefore exist in various stereochemical forms. The invention relates both to the individual isomers and to mixtures thereof.

The N-dihydroindolylethyl-sulphonamides according to the invention can also exist in the form of their salts. Salts with organic or inorganic bases may be mentioned here in general.

Physiologically acceptable salts are preferred in the context of the present invention. Physiologically acceptable salts of the N-dihydroindolylethyl-sulphonamides can be metal or ammonium salts of the substances according to the invention which have a free carboxyl group. Particularly preferred salts are, for example, sodium, potassium, magnesium or calcium salts and ammonium salts which are derived from ammonia or organic amines, such as, for example, ethylamine, di- or triethylamine, di- or triethanolamine, dicyclohexylamine, dimethylaminoethanol, arginine or ethylenediamine.

Surprisingly, the substances according to the invention exhibit a platelet aggregation-inhibiting action and can be used for therapeutic treatment of humans and animals.

Alkyl in general represents a straight-chain or branched hydrocarbon radical with 1 to 12 carbon atoms. Lower alkyl with 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general represents a straight-chain or branched hydrocarbon radical with 2 to 12 carbon atoms or one or more, preferably with one or two, double bonds. A lower alkenyl radical with 2 to about 6 carbon atoms and one double bond is preferred. An alkenyl radical with 2 to 4 carbon atoms and one double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

Cycloalkyl in general represents a cyclic hydrocarbon radical with 5 to 8 carbon atoms. The cyclopentane and the cyclohexane ring are preferred. Examples which may be mentioned are cyclopentyl, cyclohexyl, cycloheptyl and cyclooctyl.

Alkoxy in general represents a straight-chain or branched hydrocarbon radical which has 1 to 12 carbon atoms and is bonded via an oxygen atom. Lower alkoxy with 1 to about 6 carbon atoms is preferred. An alkoxy radical with 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy and isooctoxy. octoxy.

Alkylthio in general represents a straight-chain or branched hydrocarbon radical which has 1 to 12 carbon atoms and is bonded via a sulphur atom. Lower alkylthio with 1 to about 6 carbon atoms is preferred. An alkylthio radical with 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Aryl in general represents an aromatic radical with 6 to about 12 carbon atoms. Preferred aryl radicals are phenyl, naphthyl and biphenyl.

Aralkyl in general represents an aryl radical which has 7 to 14 carbon atoms and is bonded via an alkylene chain. Aralkyl radicals with 1 to 6 carbon atoms in the aliphatic part and 6 to 12 carbon atoms in the aromatic part are preferred. The following aralkyl radicals may be mentioned as examples: benzyl, naphthylmethyl, phenethyl and phenylpropyl.

Alkoxycarbonyl can be represented, for example, by the formula

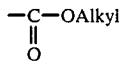

Alkyl here represents a straight-chain or branched hydrocarbon radical with 1 to 12 carbon atoms. Lower alkoxycarbonyl with 1 to about 6 carbon atoms in the alkyl part is preferred. Alkoxycarbonyl with 1 to 4 carbon atoms in the alkyl part is particularly preferred. The following alkoxycarbonyl radicals may be mentioned as examples: methoxycarbonyl, ethoxycarbonyl, propoxycarbonyl, isopropoxycarbonyl, butoxycarbonyl and isobutoxycarbonyl.

Carboxyalkyl in general represents a straight-chain or branched hydrocarbon radical which has 1 to 12 carbon atoms and is substituted by a carboxyl group. Carboxylower alkyl with 1 to about 6 carbon atoms is preferred. Examples which may be mentioned are: carboxymethyl, 1-carboxyethyl, 1-carboxypropyl, 1-carboxybutyl, 1-carboxypentyl, 1-carboxyhexyl, 2-carboxyethyl, 2-carboxypropyl, 2-carboxybutyl, 3-carboxypropyl, 3-carboxybutyl, 4-carboxybutyl, 2-carboxy-1-propyl and 1-carboxy-1-propyl.

Alkoxycarbonylalkyl in general represents a straight-chain or branched hydrocarbon radical which has 1 to 12 carbon atoms and is substituted by an alkoxycarbonyl group, alkoxycarbonyl having the abovementioned meaning. Lower alkoxycarbonyl-lower alkyl with in each case 1 to about 6 carbon atoms in each alkyl part is preferred. Examples which may be mentioned are: methoxycarbonylmethyl, ethoxycarbonylmethyl, propoxycarbonylmethyl, butoxycarbonylmethyl, isopropoxycarbonylmethyl, isobutoxycarbonylmethyl, 1-methoxycarbonylethyl, 1-ethoxycarbonylethyl, 1-propoxycarbonylethyl, 1-butoxycarbonylethyl, 1-isopropoxycarbonylethyl, 1-isobutoxycarbonylethyl, 2-methoxycarbonylethyl, 2-ethoxycarbonylethyl, 2-propoxycarbonylethyl, 2-butoxycarbonylethyl, 2-isopropoxycarbonylethyl, 2-isobutoxycarbonylethyl, 2-methoxycarbonyl-2-propyl, 2-ethoxycarbonyl-2-propyl, 2-propoxycarbonyl-2-propyl, 2-butoxycarbonyl-2-propyl, 2-isopropoxycarbonyl-2-propyl, 2-isobutoxycarbonyl-2-propyl, 1-methoxycarbonyl-2-propyl, 1-methoxycarbonyl-2-propyl, 1-propoxycarbonyl-2-propyl, 1-butoxycarbonyl-2-propyl, 1-isopropoxycarbonyl-2-propyl, 1-isobutoxycarbonyl-2-propyl, 3-methoxycarbonylpropyl, 3-ethoxycarbonylpropyl, 3-propoxycarbonylpropyl, 3-butoxycarbonylpropyl, 3-isopropoxycarbonylpropyl and 3-isobutoxycarbonylpropyl.

Halogen in general represents fluorine, chlorine, bromine or iodine, preferably fluorine, chlorine or bromine. Halogen particularly preferably represents fluorine or chlorine.

Preferred compounds of the general formula (I) are those in which $R^1$ represents hydrogen, fluorine, chlorine, bromine, trifluoromethyl, carboxyl or lower alkoxycarbonyl, or represents a group of the formula —S(O)$_m$R$^5$, wherein
$R^5$ denotes lower alkyl or phenyl and
m denotes the number 0 or 2, or
$R^1$ represents a group of the formula

wherein
$R^6$ and $R^7$ are identical or different and denote hydrogen, lower alkyl, phenyl, benzyl or acetyl, or
$R^1$ represents a group of the formula —OR$^8$,
wherein
$R^8$ denotes hydrogen, lower alkyl, phenyl, benzyl, phenylsulphonyl, methylsulphonyl, ethylsulphonyl or trifluoromethyl, or
$R^1$ represents lower alkyl, lower alkenyl, cyclopentyl or cyclohexyl, optionally substituted by carboxyl, methoxycarbonyl, ethoxycarbonyl, fluorine, chlorine, bromine, hydroxyl, lower alkoxy or cyano,
$R^2$ represents phenyl, which is optionally mono-, dior trisubstituted by fluorine, chlorine, bromine, cyano, trifluoromethyl, trifluoromethoxy, trifluoromethylthio, lower alkyl, carboxymethyl, carboxyethyl, methoxycarbonylmethyl, ethoxycarbonylmethyl, methoxycarbonylethyl, ethoxycarbonylethyl, lower alkoxy, lower alkylthio, hydroxyl, carboxyl, lower alkoxycarbonyl, phenyl, phenoxy, benzyloxy or benzylthio, or is substituted by the group of the formula

wherein
$R^6$ and $R^7$ have the meaning already given,
$R^3$ represents hydrogen or lower alkyl and
$R^4$ represents hydrogen, or
$R^3$ and $R^4$ together bond a carbonyl oxygen,
and salts thereof.

Particularly preferred compounds of the general formula (I) are those in which
$R^1$ represents hydrogen, fluorine, chlorine, bromine, trifluoromethyl, methylthio, ethylthio, methylsulphonyl, ethylsulphonyl, phenylthio, phenylsulphonyl, amino, dimethylamino, diethylamino or acetylamino, or represents a group of the formula —OR$^8$,
wherein
$R^8$ denotes hydrogen, $C_1$–$C_4$-alkyl, phenyl or benzyl, or
$R^1$ represents $C_1$–$C_4$-alkyl,
$R^2$ represents phenyl, which can be mono- or di-substituted by identical or different substituents selected from the group consisting of fluorine, chlorine, bromine, cyano, trifluoromethyl, trifluoromethoxy, $C_1$–$C_4$-alkyl, $C_1$–$C_4$-alkoxy, methylthio, hydroxyl, methoxycarbonyl, ethoxycarbonyl, dimethylamino, acetylamino and diethylamino,
$R^3$ represents hydrogen or $C_1$–$C_4$-alkyl and
$R^4$ represents hydrogen, or
$R^3$ and $R^4$ together bond a carbonyl oxygen,
and salts thereof.

Especially preferred compounds of the general formula (I) are those in which $R^1$ represents hydrogen, fluorine, chlorine, methyl, methoxy or hydroxyl, $R^2$ represents phenyl, which is substituted by fluorine, chlorine, trifluoromethyl, methyl, ethyl, propyl, isopropyl or methoxy, $R^3$ represents hydrogen or methyl and $R^4$ represents hydrogen, or $R^3$ and $R^4$ together bond a carbonyl oxygen, and salts thereof.

The following N-dihydroindolylethyl-sulphonamides may be mentioned as examples: N-[2-[1-(2-carboxyethyl)-2,3-dihydro-1H-indol-3-yl]ethyl]enzenesulphonamide, N-[2-[1-(2-carboxyethyl)-2,3-dihydro-1H-indol-3-yl]ethyl]-(4-fluorophenyl)sulphonamide, N-[2-[1-(2-carboxyethyl)-2,3-dihydro-2-methyl-1H-indol-3-yl]ethyl]-(4-chlorophenyl)sulphonamide, N-[2-[1-(2-carboxyethyl)-2,3-dihydro-2-methyl-1H-indol-3-yl]ethyl]-(4-fluorophenyl)sulphonamide, N-[2-[1-(2-carboxyethyl)-2,3-dihydro-5-fluoro-2-methyl-1H-indol-3-yl]ethyl]-(4-fluorophenyl)sulphonamide, N-[2-[1-(2-carboxyethyl)-2,3-dihydro-2-oxo-1H-indol-3-yl]ethyl]benzenesulphonamide, N-[2-[1-(2-carboxyethyl)-2,3-dihydro-2-oxo-1H-indol-3-yl]ethyl]-(4-chlorophenyl)sulphonamide and N-[2-[1-(2-carboxyethyl)-2,3-dihydro-2-oxo-1H-indol-3-yl]ethyl]-(4-fluorophenyl)sulphonamide.

In the context of the present invention, the N-dihydroindolylethyl-sulphonamides (Ia) correspond to the formula

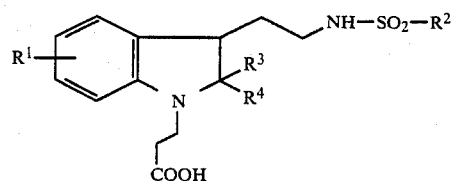

in which $R^1$ and $R^2$ have the meaning given, $R^3$ represents hydrogen or alkyl and $R^4$ represents hydrogen.

In the context of the present invention, the N-dihydroindolylethyl-sulphonamides (Ib) correspond to the formula

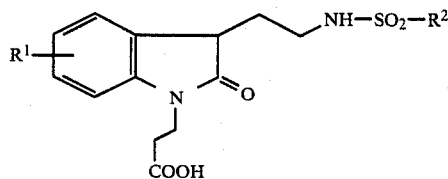

in which $R^1$ and $R^2$ have the meaning given.

A process has been found for the preparation of N-dihydroindolylethyl-sulphonamides of the general formula (Ia)

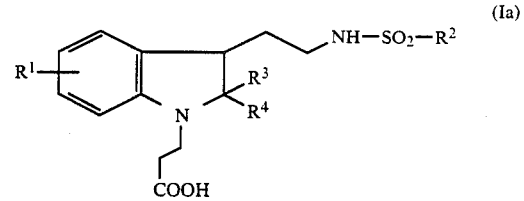

in which $R^1$ represents hydrogen, halogen, trifluoromethyl, carboxyl or alkoxycarbonyl, or represents a group of the formula $-S(O)_m R^5$, $R^5$ denotes alkyl or aryl and m denotes one of the numbers 0, 1 or 2, or $R^1$ represents a group of the formula

wherein $R^6$ and $R^7$ are identical or different and denote hydrogen, alkyl, aryl, aralkyl or acyl, or $R^1$ represents a group of the formula $-OR^8$, wherein $R^8$ denotes hydrogen, alkyl, aryl, aralkyl, alkylsulphonyl, arylsulphonyl, aralkylsulphonyl or trifluoromethyl, or $R^1$ represents alkyl, alkenyl or cycloalkyl, optionally substituted by carboxyl, alkoxycarbonyl, halogen, hydroxyl, alkoxy, alkylthio or cyano, $R^2$ represents aryl, which is optionally substituted by up to 5 substituents selected from the group consisting of halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy and benzylthio or by a group of the formula

in which $R^6$ and $R^7$ have the abovementioned meaning, $R^3$ represents hydrogen or alkyl and $R^4$ represents hydrogen, and salts thereof, which is characterized in that N-indolylethyl-sulphonamides of the general formula (II)

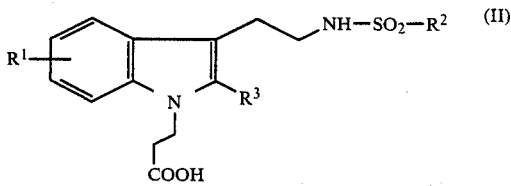

in which $R^1$, $R^2$ and $R^3$ have the abovementioned meaning, or salts thereof, are hydrogenated, if appropriate in the presence of an inert organic solvent, in the presence of an acid and a reducing agent, if appropriate isomers are resolved in the customary manner and, in the case of the preparation of the salts, the products are reacted with a corresponding base.

The process according to the invention can be illustrated by the following equation:

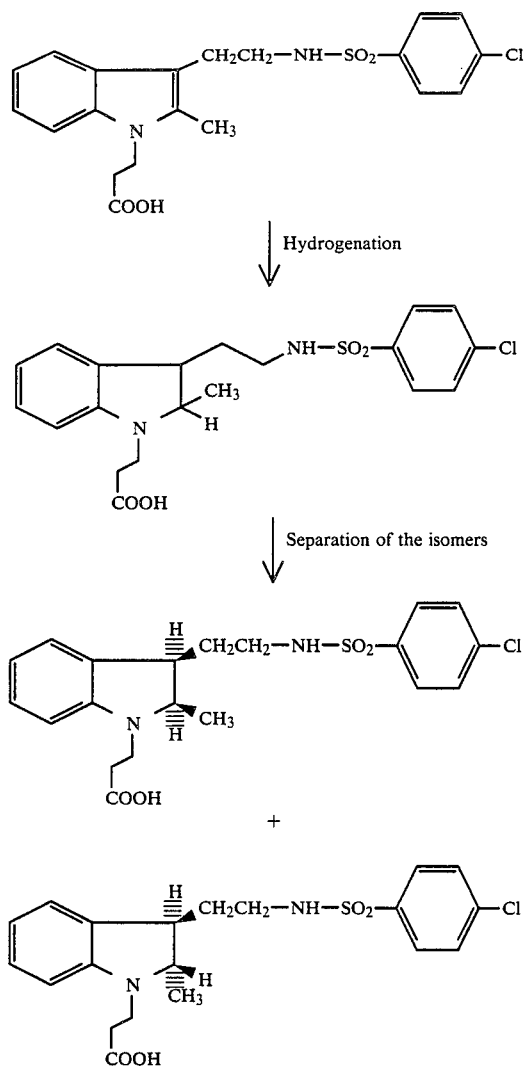

Possible solvents for the hydrogenation are inert organic solvent which are not changed under the reaction conditions. These include, preferably, ethers, such as diethyl ether, dioxane or tetrahydrofuran, or acetic acid, trifluoroacetic acid, methanesulphonic acid or trifluoromethanesulphonic acid. It is also possible to employ mixtures of the solvents mentioned.

Acids which can be employed are the customary organic acids. These include, preferably, carboxylic acids, such as, for example, acetic acid, propionic acid, chloroacetic acid, dichloroacetic acid or trifluoroacetic acid, or sulphonic acids, such as, for example, methanesulphonic acid, ethanesulphonic acid, toluenesulphonic acid, benzenesulphonic acid or trifluoromethanesulphonic acid.

Possible reducing agents for the hydrogenation according to the invention are the customary reducing agents. These include, preferably, hydrides, such as, for example, sodium borohydride, sodium cyanoborohydride, tetrabutylammonium borohydride, tetrabutylammonium cyanoborohydride, tributyl-tin hydride, triethylsilane, dimethylphenylsilane or triphenylsilane.

The hydrogenation is in general carried out in a temperature range from −40° C. to +80° C., preferably from −20° C. to +60° C.

The process according to the invention is in general carried out under normal pressure. However, it is also possible to carry out the process under reduced pressure or under increased pressure (for example in a pressure range from 0.5 to 5 bar).

In general, 1 to 5, preferably 1 to 1.5, mol of the reducing agent are employed per mol of the N-indolylethyl-sulphonamide (II). Molar amounts of the reactants are particularly preferably employed.

In carrying out the process according to the invention, the compounds are in general obtained as isomer mixtures, which can be resolved into the individual isomers by customary methods, such as, for example, crystallization or, preferably, chromatography [E. L. Eliel, "Stereochemistry of Carbon Compounds", McGraw Hill (1962); W. C. Still, M. Kahn, A. Mitra, J. Org. Chem. 43, 2923 (1978)].

The process according to the invention can be carried out, for example, as follows:

The N-indolylethylsulphonamide is dissolved in an inert solvent and the reducing agent is then added in portions. When the reaction has ended, the mixture is worked up by extraction and/or chromatography.

A process has also been found for the preparation of N-dihydroindolylethyl-sulphonamides of the general formula (Ib)

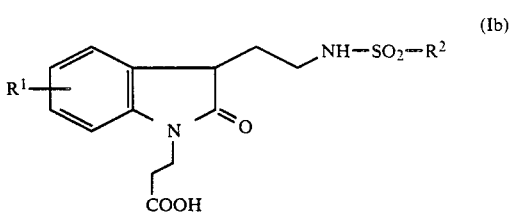

(Ib)

in which
R$^1$ represents hydrogen, halogen, trifluoromethyl, carboxyl or alkoxycarbonyl, or represents a group of the formula —S(O)$_m$R$^5$,
wherein
R$^5$ denotes alkyl or aryl and
m denotes one of the numbers 0, 1 or 2, or
R$^1$ represents a group of the formula

wherein
R$^6$ and R$^7$ are identical or different and denote hydrogen, alkyl, aryl, aralkyl or acyl, or
R$^1$ represents a group of the formula —OR$^8$,
wherein
R$^8$ denotes hydrogen, alkyl, aryl, aralkyl, alkylsulphonyl, arylsulphonyl, aralkylsulphonyl or trifluoromethyl, or $R^1$ represents alkyl, alkenyl or cycloalkyl, optionally substituted by carboxyl, alkoxycarbonyl, halogen, hydroxyl, alkoxy, alkylthio or cyano and $R^2$ represents aryl, which is optionally substituted by up to 5 substituents selected from the group consisting of halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy and benzylthio or by a group of the formula

in which $R^6$ and $R^7$ have the abovementioned meaning, and salts thereof, which is characterized in that N-indolylethyl-sulphonamides of the general formula (IIa)

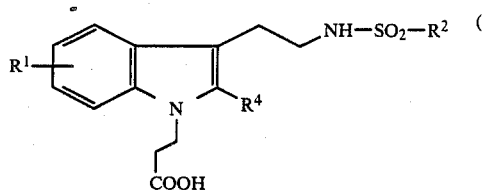

in which $R^1$ and $R^2$ have the abovementioned meaning and $R^4$ represents hydrogen, or salts thereof, are oxidized in inert solvents, if appropriate in the presence of an acid, and, in the case of the preparation of the salts, the products are reacted with a corresponding base.

The process according to the invention can be illustrated by the following equation:

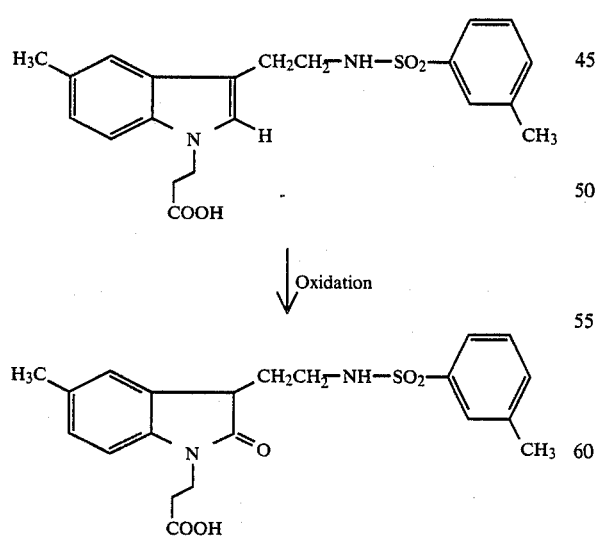

Oxidizing agents for the process according to the invention are preferably electrophilic oxidizing agents. Preferred oxidizing agents which may be mentioned are N-bromosuccinimide, halogens, such as chlorine and bromine, and dimethylsulphoxide. Bromine and dimethylsulphoxide are particularly preferred.

Oxidation with dimethylsulphoxide in inert solvents in the presence of acids is particularly preferred.

Possible solvents here are water or the customary inert organic solvents which do not change under the reaction conditions. These include, preferably: alcohols, such as methanol, ethanol, propanol or isopropanol, or ethers, such as diethyl ether, dioxane, tetrahydrofuran or glycol mono- or glycol dimethyl ether, or hydrocarbons, such as, for example, benzene, toluene, xylene or petroleum fractions (about $C_5$ to $C_{12}$), or halogenohydrocarbons, such as, for example, methylene chloride, chloroform, carbon tetrachloride or 1,2-dichloroethane, or acetic acid, trifluoroacetic acid or dimethylsulphoxide.

If appropriate, the oxidation can be carried out in the presence of acids.

Acids which can be employed are the customary inorganic or organic acids. These include, preferably, inorganic acids, such as hydrochloric acid, hydrobromic acid, hydriodic acid, sulphuric acid or phosphoric acid, or organic acids, such as acetic acid, trifluoroacetic acid, chloroacetic acid, dichloroacetic acid, trichloroacetic acid or sulphonic acids, such as methanesulphonic acid, ethanesulphonic acid, benzenesulphonic acid, toluenesulphonic acid or trifluoromethanesulphonic acid.

The oxidation is in general carried out in a temperature range from 0° C. to 100° C., preferably from 20° C. to 60° C.

The process according to the invention is in general carried out under normal pressure, but it is also possible to carry out the process under reduced pressure or under increased pressure (for example in a pressure range from 0.5 to 5 bar).

In general, 1 to 2 mol, preferably 1 to 1.5 mol, of oxidizing agent are employed per mol of N-indolylethylsulphonamide (IIa). Molar amounts of the reactants are especially preferably used.

The process according to the invention can be carried out, for example, as follows:

The N-indolylethylsulphonamide is suspended in dimethylsulphoxide, which is simultaneously the diluent and oxidizing agent, and an acid is added. When the reaction has ended, the mixture is worked up by extraction.

The N-indolylethyl-sulphonamides of the general formula (II) employed as starting substances and salts thereof are novel compounds.

They can be prepared by a process in which indolylethyl-amines of the general formula (III)

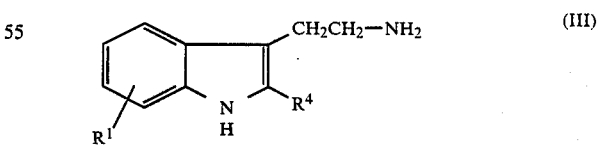

in which $R^1$ represents hydrogen, halogen, trifluoromethyl, carboxyl or alkoxycarbonyl, or represents a group of the formula $S(O)_m R^5$, wherein $R^5$ denotes alkyl or aryl and m denotes one of the numbers 0, 1 or 2, or $R^1$ represents a group of the formula

wherein
R$^6$ and R$^7$ are identical or different and denote hydrogen, alkyl, aryl, aralkyl or acyl, or
R$^1$ represents a group of the formula —OR$^8$,
wherein
R$^8$ denotes hydrogen, alkyl, aryl, aralkyl, alkylsulphonyl, arylsulphonyl, aralkylsulphonyl or trifluoromethyl, or
R$^1$ represents alkyl, alkenyl or cycloalkyl, optionally substituted by carboxyl, alkoxycarbonyl, halogen, hydroxyl, alkoxy, alkylthio or cyano and
R$^4$ represents hydrogen,
are reacted with sulphonic acid halides of the general formula (IV)

 (IV)

in which
R$^2$ represents aryl, which is optionally substituted by up to 5 substituents from the group comprising halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy and benzylthio or by a group of the formula

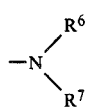

in which
R$^6$ and R$^7$ have the abovementioned meaning and
Y represents halogen,
and with acrylonitrile of the formula (V)

 (V)

in the presence of an inert solvent, if appropriate in the presence of a base, the N,N'-biscyanoethyl compounds are then hydrolyzed and, in the case of the preparation of the salts, the products are reacted with a corresponding base.

The preparation of the N-indolylethyl-sulphonamides of the formulae (II) and (IIa) used as starting substances can be illustrated by the following equation:

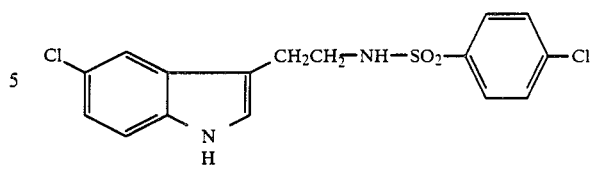

↓ + CH$_2$=CH—CN

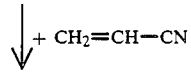

↓

Intermediate products which can be isolated are in general formed in carrying out the process. Thus, it is possible to carry out the process in several process stages. However, it can also be possible to combine various process steps.

The indolylethylamines of the general formula (III), the sulphonic ccid halides of the general formula (IV) and acrylonitrile of the formula (V) are known per se and can be prepared by methods which are known per se (Houben-Weyls "Methoden der organischen Chemie" ("Methods of Organic Chemistry") Volume IX, 407 et seq. and 547 et seq. (1959); The Chemistry of Indoles, Academic Press 1970; W. J. Honlihan, Indoles Part II, John Wiley & Sons, 1972).

Solvents for the process can be inert organic solvents which do not change under the reaction conditions. These include, preferably, alcohols, such as, for example, methanol, ethanol, propanol or isopropanol, or ethers, such as, for example, diethyl ether, dioxane or tetrahydrofuran, or halogenohydrocarbons, such as, for example, methylene chloride, chloroform, carbon tetrachloride, dichloroethylene or trichloroethylene, or acetic acid, toluene, acetonitrile, nitromethane, dimethylformamide, hexamethylphosphoric acid triamide, pyridine and acetone. It is of course also possible to employ mixtures of the solvents.

The bases employed can be the customary basic compounds for basic reactions. These include, preferably, alkali metal and alkaline earth metal hydroxides or carbonates, such as, for example, lithium, sodium, potassium, calcium or barium hydroxide and sodium or potassium carbonate, alkali metal alcoholates, such as, for example, sodium methanolate and ethanolate or potassium methanolate or ethanolate, or organic bases, such as, for example, triethylamine, pyridine or 1-methylpiperidine, benzyltrimethylammonium hydroxide or tetrabutylammonium hydroxide. The process is in general carried out in the temperature range from −20° C. to +100° C., preferably from 0° C. to 80° C.

The process is in general carried out under normal pressure. However, it is also possible to carry out the process under reduced or increased pressure (for example in a pressure range from 0.5 to 10 bar).

In general, 1 to 5 mol, preferably 1 to 2 mol and particularly preferably 1 mol, of sulphonic acid halide are employed per mol of the indolylethylamine. Acrylonitrile is in general employed in an amount of 1 to 10 mol, preferably 1 to 5 mol and particularly preferably 3 mol, per mol of the indolylethylamine.

The hydrolysis is in general carried out in the presence of bases, preferably alkali metal or alkaline earth metal hydroxides or alcoholates. Bases which are preferably used are bases such as alkali metal or alkaline earth metal hydroxides or alkali metal alcoholates, preferably lithium, sodium, potassium, calcium or barium hydroxide or sodium or potassium methylate or ethylate.

In general, 1 to 100 mol, preferably 2 to 50 mol, of the base are employed in the hydrolysis per mol of the N,N'-biscyanoethyl compound.

Examples of indolylethylamines which can be used according to the invention are: 2-(5-methyl-1H-indol-3-yl)ethylamine, 2-(5-methoxy-1H-indol-3-yl)ethylamine, 2-(5-fluoro-1H-indol-3-yl)ethylamine and 2-(5-chloro-1H-indol-3-yl)ethylamine.

Examples of sulphonic acid halides which can be used according to the invention are: 4-chlorophenylsulphonyl chloride, 4-fluorophenylsulphonyl chloride, 4-methylphenylsulphonyl chloride, 4-toluenesulphonyl chloride and 4-methoxyphenylsulphonyl chloride.

Examples of N-indolylethyl-sulphonamides which can be used according to the invention are: N-[2-[1-(2-carboxyethyl)-1H-indol-3-yl]ethyl]benzenesulphonamide, the sodium salt of N-[2-[1-(2-carboxyethyl)-1H-indol-3-yl]ethyl]benzenesulphonamide, the triethylammonium salt of N-[2-[1-(2-carboxyethyl)-1H-indol-3-yl]ethyl]benzenesulphonamide, the triethylammonium salt of N-[2-[1-(2-carboxyethyl)-1H-indol-3-yl]ethyl]-(4-fluorophenyl)sulphonamide, N-[2-[1-(2-carboxyethyl)-2-methyl-1H-indol-3-yl]ethyl]-(4-chlorophenyl)sulphonamide, the triethylammonium salt of N-[2-[1-(2-carboxyethyl)-2-methyl-1H-indol-3-yl]ethyl]-(4-chlorophenyl)sulphonamide and N-[2-[1-(2-carboxyethyl)-5-fluoro-2-methyl-1H-indol-3-yl]ethyl]-(4-fluorophenyl)-sulphonamide.

The new N-dihydroindolylethyl-sulphonamides and salts thereof can be used as active compounds in medicaments. The active compounds have, for example, a platelet aggregation-inhibiting and thromboxan $A_2$-antagonistic action. They can preferably be used for the treatment of thromboses, thromboembolisms and ischaemias, as antiasthmatics and as antiallergics.

The new active compounds can be converted in a known manner into the customary formulations, such as tablets, dragees, pills, granules, aerosols, syrups, emulsions, suspensions or solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the dosage range stated.

The formulations are prepared, for example, by extending the active compounds with solvents and/or excipients, if appropriate using emulsifying agents and/or dispersing agents, and, for example, in the case of the use of water as the diluent, organic solvents can be used as auxiliary solvents if appropriate.

Examples of auxiliaries which may be mentioned are: water, non-toxic organic solvents, such as paraffins (for example petroleum fractions), vegetable oils (for example groundnut oil/sesame oil) and alcohols (for example: ethyl alcohol and glycerol), excipients, such as, for example, natural rock powders (for example kaolins, aluminas, talc and chalk), synthetic rock powders (for example highly disperse silicic acid and silicates), sugars (for example sucrose, lactose and glucose), emulsifying agents (for example polyoxyethylene fatty acid esters and polyoxyethylene fatty alcohol ethers alkyl sulphonates, arylsulphonates), dispersing agents (for example lignin-sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral use, tablets can of course also contain additives, such as sodium citrate, calcium carbonate and dicalcium phosphate, together with various adjuvants, such as starch, preferably potato starch, gelatine and the like, in addition to the excipients mentioned. Lubricants, such as magnesium stearate, sodium lauryl-sulphate and talc, can furthermore be co-used for tablet-making. In the case of aqueous suspensions, flavour-improving agents or dyestuffs can be added to the active compounds, in addition to the abovementioned auxiliaries.

In the case of parenteral use, solutions of the active compounds can be employed, using suitable liquid excipients.

In general, it has proved advantageous, in the case of intravenous administration, to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular to do so as a function of the body weight or the nature of the mode of administration, of the individual behaviour towards the medicament, of the nature of its formulation and the time or interval at which administration takes place. Thus it can in some cases be necessary to manage with less than the abovementioned minimum amount, whilst in other cases the upper limit mentioned must be exceeded. Where relatively large amounts are administered, it may be advisable to divide these into several individual doses over the course of the day.

PREPARATION EXAMPLES

EXAMPLE 1

N-[2-[1-(2-Carboxyethyl)-2,3-dihydro-1H-indol-3-yl]ethyl]benzenesulphonamide

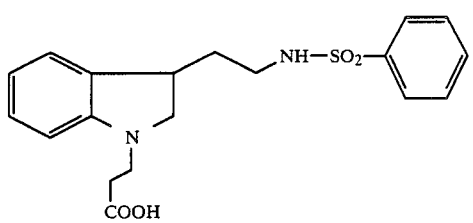

0.95 g (2 mmol of the triethylammonium salt of N-[2-[1-(2-carboxyethyl)-1H-indol-3-yl]ethyl]benzenesulphonamide are dissolved in 10 ml of trifluoroacetic acid at room temperature and 0.23 g (2 mmol) of triethylsilane are added. After the mixture has stood for 10 hours, it is diluted with 2N sodium hydroxide solution and extracted with ethyl acetate. The aqueous phase is rendered acid with 2N sulphuric acid and extracted twice with ethyl acetate. The combined ethyl acetate phases are dried with sodium sulphate and evaporated. After drying under a high vacuum, the residue is purified on 100 g of silica gel (Merck, 0.63–0.2 mm) with a mixture of methylene chloride and methanol in a ratio of 96 to 4. A fraction which contains 0.68 g of a viscous oily product is thus obtained ($R_f=0.12$, CH$_2$Cl$_2$:ethyl acetate=100:2).

To prepare the hydrochloride, the product is dissolved in acetone and 3 ml of 1N hydrochloric acid are added. After thorough evaporation in vacuo, 0.7 g (85% of theory) of a solid residue is obtained.

Melting point: 70°–80° C.

EXAMPLE 2

N-[2-[1-(2-Carboxyethyl)-2,3-dihydro-1H-indol-3-yl]ethyl]-(4-fluorophenyl)sulphonamide

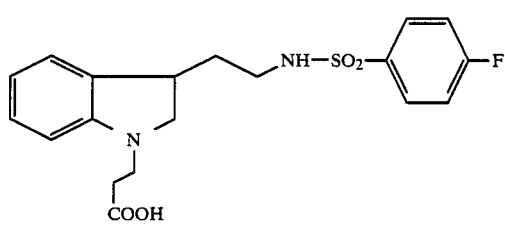

0.75 g (1.9 mmol) of N-[2-[1-(2-carboxyethyl)-1H-indol-3-yl]ethyl]-(4-fluorophenyl)sulphonamide are reduced with triethylsilane analogously to Example 1. 0.58 g of a viscous oily product is thus obtained ($R_f=0.18$, CH$_2$Cl$_2$:ethyl acetate=100:2). After conversion of the product into its hydrochloride (analogously to Example 1), 0.62 g (76% of theory) of a solid residue is obtained.

Melting point: 70°–80° C.

EXAMPLE 3

N-[2-[1-(2-Carboxyethyl)-2,3-dihydro-2-methyl-1H-indol-3-yl]ethyl]-(4-chlorophenyl)sulphonamide

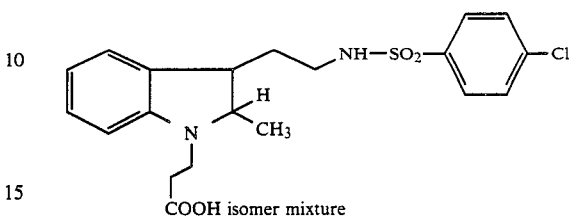

COOH isomer mixture 1 g of sodium cyanoborohydride is added in portions to 0.9 g (2.1 mmol) of N-[2-[1-(2-carboxyethyl)-2-methyl-1H-indol-3-yl]ethyl]-(4-chlorophenyl)sulphonamide in 10 ml of trifluoroacetic acid at 0° C. After the reaction solution has been stirred at 0° to 5° C. for 2 hours, it is diluted with ethyl acetate and extracted three times with saturated sodium chloride solution. The ethyl acetate phase is dried with sodium sulphate and evaporated thoroughly in vacuo. The residue is chromatographed on silica gel (Merck, 0.04 to 0.063 mm) with a mixture of methylene chloride and methanol in a ratio of 96 to 4. A fraction which, after evaporation, gives 0.8 g of a viscous oily product is thus obtained ($R_f=0.3$, CH$_2$Cl$_2$:glacial acetic acid=100:2). This viscous oil is converted into its hydrochloride analogously to Example 1: 0.82 g (85% of theory) of a solid residue.

Melting point: 75°–80° C.

EXAMPLE 4

N-[2-[1-(2-Carboxyethyl)-2,3-dihydro-2-methyl-1H-indol-3-yl]ethyl]-(4-fluorophenyl)sulphonamide

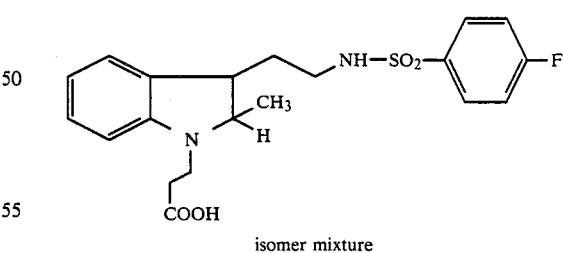

isomer mixture 1 g (2.5 mmol) of N-[2-[1-(2-carboxyethyl)-2-methyl-1H-indol-3-yl]ethyl]-(4-fluorophenyl)sulphonamide is reduced with sodium cyanoborohydride analogously to Example 3. 0.85 g of a viscous oily product is thus obtained ($R_f=0.32$, CH$_2$Cl$_2$:glacial acetic acid=100:2), which is converted into its hydrochloride analogously to Example 1: 0.9 g (81% of theory) of a solid residue.

Melting point: 75°–80° C.

EXAMPLE 5 AND EXAMPLE 6

N-[2-[1-(2-Carboxyethyl)-5-fluoro-2,3-r-dihydro-2-c-methyl-1H-indol-3-yl]ethyl]-(4-fluorophenyl)sulphonamide

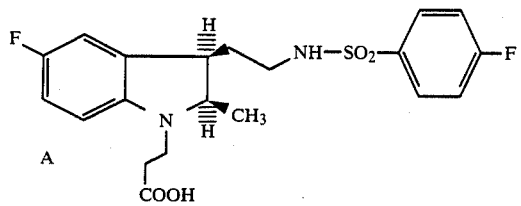

A and
N-[2-[1-(2-carboxyethyl)-5-fluoro-2,3-r-dihydro-2-t-methyl-1H-indol-3-yl]ethyl]-(4-fluorophenyl)sulphonamide

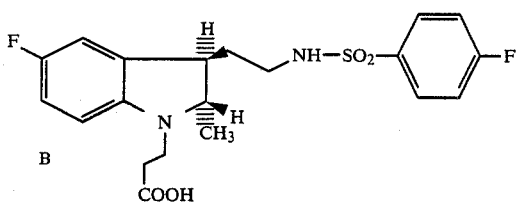

B 5.47 g (0.013 mol) of N-[2-[1-(2-carboxyethyl)-5-fluoro-2-methyl-1H-indol-3-yl]ethyl]-(4-fluorophenyl)-sulphonamide are reduced with sodium cyanoborohydride analogously to Example 3. Column chromatography on 400 g of silica gel (Merck, 0.04–0.063 mm) with a 100:1 mixture of methylene chloride with glacial acetic acid gives two fractions, the first of which gives, after evaporation, 0.47 g of isomer A ($R_f=0.5$, $CH_2Cl_2$:glacial acetic acid=100:2). The second fraction gives, after evaporation, 2.28 g of isomer B ($R_f=0.42$ g, $CH_2Cl_2$:glacial acetic acid=100:2). The isomers A and B thus obtained are converted into their hydrochlorides analogously to Example 1. 2.35 g (39% of theory) of solid hydrochloride of isomer B and 0.53 g (9% of theory) of solid hydrochloride of isomer A are thereby obtained.

Melting point of isomer A: 80°–90° C.
Melting point of isomer B: 58°–70° C.

EXAMPLE 7

N-[2-[1-(2-Carboxyethyl)-2,3-dihydro-2-oxo-1H-indol-3-yl]ethyl]benzenesulphonamide

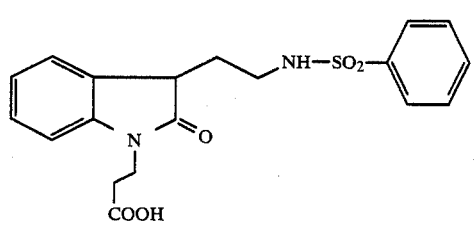

0.74 g (1.56 mmol) of the triethylammonium salt of N-[2-[1-(2-carboxyethyl)-1H-indol-3-yl]ethyl]benzenesulphonamide are suspended in 8 ml of dimethylsulphoxide, and 4 ml of concentrated hydrochloric acid are added. The clear solution is stirred at 50° C. for 3 hours. It is then diluted with water and extracted with ethyl acetate. The ethyl acetate phase is washed twice more with water, dried with sodium sulphate and evaporated. 0.57 g (94% of theory) of a solid product is thus obtained.

$R_f=0.34$, $CH_2Cl_2$:$CH_3OH=9:1$.
Melting point: 50°–60° C.

EXAMPLE 8

N-[2-[1-(2-Carboxyethyl)-2,3-dihydro-2-oxo-1H-indol-3-yl]ethyl]-(4-chlorophenyl)sulphonamide

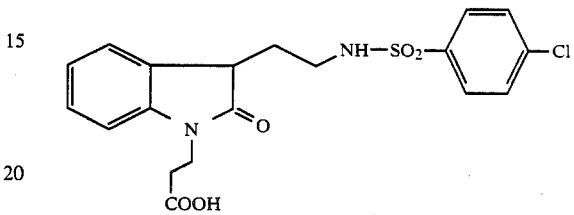

1.72 g (3.4 mmol) of the triethylammonium salt of N-[2-[1-(2-carboxyethyl)-1H-indol-3-yl]ethyl]-(4-chlorophenyl)sulphonamide are oxidized analogously to Example 7. 1.4 g (97% of theory) of a solid product are thus obtained.

$R_f=0.44$, $CH_2Cl_2$:$CH_3OH=9:1$.
Melting point: 60°–70° C.

EXAMPLE 9

N-[2-[1-(2-Carboxyethyl)-2,3-dihydro-2-oxo-1H-indol-3-yl]ethyl]-(4-fluorophenyl)sulphonamide

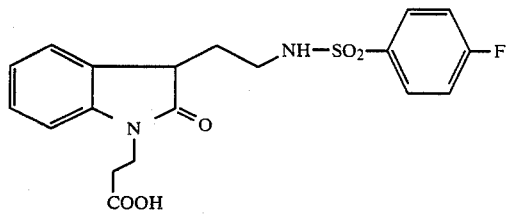

3 g (7.7 mmol o& N-[2-[1-(2-carboxyethyl)-1H-indol-3-yl]ethyl-(4-fluorophenyl)sulphonamide are oxidized analogously to Example 7. 3 g (96% of theory) of a solid product are thus obtained.

$R_f=0.36$, $CH_2Cl_2$:$CH_3OH=9:1$.
Melting point: 60°–70° C.

EXAMPLE 10

Use Example

To determine the platelet aggregation-inhibiting action, blood from healthy volunteers of both sexes was used. One part of 3.8% strength aqueous sodium citrate solution, as an anticoagulant, was mixed with 9 parts of blood. Platelet-rich citrated plasma (PRP) is obtained from this blood by centrifugation (Jurgens/Beller, Klinische Methoden der Blutgerinnungsanalyse (Clinical Methods of Blood Coagulation Analysis); Thieme Verlag, Stuttgart, 1959).

For these investigations, 0.8 ml of PRP and 0.1 ml of the active compound solution were preincubated in a waterbath at 37° C. The platelet aggregation was then determined by the turbidometric method (Born, G. V. R., J. Physiol. (London), 162, 67, 1962) in an aggregometer at 37° C. (Therapeutische Berichte 47, 80–86, 1975). For this, 0.1 ml of collagen, an aggregation-inducing agent, was added to the preincubated sample. The change in optical density in the sample of PRP was recorded over a period of 6 minutes and the deflection was determined after 6 minutes. The percentage inhibition here in comparison with the control is calculated.

| N—Dihydroindolylethyl-sulphonamides according to Example No. | Limit concentration for inhibition (mg/l) |
|---|---|
| 1 | 10 to 3.0 |
| 2 | 1 to 0.3 |
| 3 | 1 to 0.3 |
| 4 | 0.3 to 0.1 |
| 5 | 0.1 to 0.01 |
| 7 | 1 to 0.1 |
| 8 | 0.1 to 0.03 |

We claim:

1. An N-dihydroindolylethyl-sulphonamide of the formula

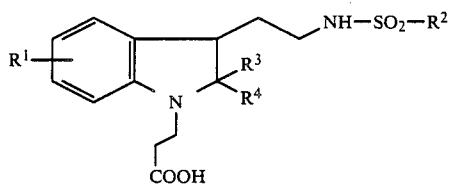

in which
$R^1$ represents hydrogen, halogen, carboxyl or alkoxycarbonyl, or represents a group of the formula $-S(O)_mR^5$,
wherein
$R^5$ denotes alkyl or aryl and
m denotes one of the numbers 0, 1 or 2, or
$R^1$ represents a group of the formula

wherein
$R^6$ and $R^7$ are identical or different and denote hydrogen, alkyl, aryl, aralkyl or acetyl, or
$R^1$ represents a group of the formula $-OR^8$,
wherein
$R^8$ denotes hydrogen, alkyl, aryl, aralkyl, alkylsulphonyl, arylsulphonyl, aralkylsulphonyl or trifluoromethyl, or
$R^1$ represents alkyl, alkenyl or cycloalkyl, optionally substituted by carboxyl, alkoxycarbonyl, halogen, hydroxyl, alkoxy, alkylthio or cyano,
$R^2$ represents aryl, which is optionally substituted by up to 5 substituents selected from the group consisting of halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy and benzylthio or by a group of the formula

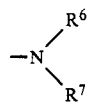

in which
$R^6$ and $R^7$ have the abovementioned meaning,
$R^3$ represents hydrogen or alkyl and
$R^4$ represents hydrogen, or
$R^3$ and $R^4$ together bond a carbonyl oxygen,
and salts thereof.

2. An N-dihydroindolylethyl-sulphonamide according to claim 1,
wherein
$R^1$ represents hydrogen, fluorine, chlorine, bromine, carboxyl or alkoxycarbonyl having 1 to 6 carbon atoms in the alkoxy portion, or represents a group of the formula $-S(O)_mR^5$,
wherein
$R^5$ denotes alkyl having 1 to 6 carbon atoms or phenyl and
m denotes the number 0 or 2, or
$R^1$ represents a group of the formula

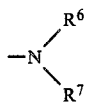

wherein
$R^6$ and $R^7$ are identical or different and denote hydrogen, alkyl having 1 to 6 carbon atoms, phenyl, benzyl or acetyl, or
$R^1$ represents a group of the formula $-OR^8$,
wherein
$R^8$ denotes hydrogen, alkyl having 1 to 6 carbon atoms, phenyl, benzyl, phenylsulphonyl, methylsulphonyl, ethylsulphonyl or trifluoromethyl, or
$R^1$ represents alkyl having 1 to 6 carbon atoms, alkenyl having 2 to 6 carbon atoms, cyclopentyl or cyclohexyl, optionally substituted by carboxyl, methoxycarbonyl, ethoxycarbonyl, fluorine, chlorine, bromine, hydroxyl, alkoxy having 1 to 6 carbon atoms or cyano,
$R^2$ represents phenyl, which is optionally mono-, di- or trisubstituted by fluorine, chlorine, bromine, cyano, trifluoromethyl, trifluoromethoxy, trifluoromethylthio, alkyl having 1 to 6 carbon atoms, carboxymethyl, carboxyethyl, methoxycarbonylmethyl, ethoxycarbonylmethyl, methoxycarbonylethyl, ethoxycarbonylethyl, alkoxy having 1 to 6 carbon atoms, alkylthio having 1 to 6 carbon atoms, hydroxyl, carboxyl, alkoxycarbonyl having 1 to 6 carbon atoms in the alkoxy portion, phenyl, phenoxy, benzyloxy or benzylthio, or is substituted by the group of the formula

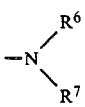

wherein
$R^6$ and $R^7$ have the meaning already given,
$R^3$ represents hydrogen or alkyl having 1 to 6 carbon atoms and R$^4$ represents hydrogen, or R$^3$ and R$^4$ together bond a carbonyl oxygen,
and salts thereof.

3. An N-dihydroindolylethyl-sulphonamide according to claim 1,
wherein
R$^1$ represents hydrogen, fluorine, chlorine, bromine, trifluoromethyl, methylthio, ethylthio, methylsulphonyl, ethylsulphonyl, phenylthio, phenylsulphonyl, amino, dimethylamino, diethylamino or acetylamino, or represents a group of the formula —OR$^8$,
wherein
R$^8$ denotes hydrogen, C$_1$–C$_4$-alkyl, phenyl or benzyl, or
R$^1$ represents C$_1$–C$_4$-alkyl,
R$^2$ represents phenyl, which can be mono- or disubstituted by identical or different substituents selected from the group consisting of fluorine, chlorine, bromine, cyano, trifluoromethyl, trifluoromethoxy, C$_1$–C$_4$-alkyl, C$_1$–C$_4$-alkoxy, methylthio, hydroxyl, methoxycarbonyl, ethoxycarbonyl, dimethylamino, acetylamino and diethylamino,
R$^3$ represents hydrogen or C$_1$–C$_4$-alkyl and
R$^4$ represents hydrogen, or
R$^3$ and R$^4$ together bond a carbonyl oxygen,
and salts thereof.

4. An N-dihydroindolylethyl-sulphonamide according to claim 1 selected from the group consisting of N-[2-[1-(2-carboxyethyl)-2,3-dihydro-1H-indol-3-yl]ethyl]benzenesulphonamide, N-[2-[1-(2-carboxyethyl)-2,3-dihydro-1H-indol-3-yl]ethyl]-(4-fluorophenyl)sulphonamide, N-[2-[1-(2-carboxyethyl)-2,3-dihydro-2-methyl-1H-indol-3-yl]ethyl]-(4-chlorophenyl)sulphonamide, N-[2-[1-(2-carboxyethyl)-2,3-dihydro-2-methyl-1H-indol-3-yl]ethyl]-(4-fluorophenyl)sulphonamide, N-[2-[1-(2-carboxyethyl)-2,3-dihydro-5-fluoro-2-methyl-1H-indol-3-yl]ethyl]-(4-fluorophenyl)sulphonamide, N-[2-[1-(2-carboxyethyl)-2,3-dihydro-2-oxo-1H-indol-3-yl]ethyl]benzenesulphonamide, N-[2-[1-(2-carboxyethyl)-2,3-dihydro-2-oxo-1H-indol-3-yl]ethyl]-(4-chlorophenyl)sulphonamide and N-[2-[1-(2-carboxyethyl)-2,3-dihydro-2-oxo-1H-indol-3-yl]ethyl]-(4-fluorophenyl)sulphonamide and salts thereof.

5. A pharmaceutical composition useful in inhibiting platelet aggregation or as a thromboxan A$_2$-antagonist comprising an effective amount of an N-dihydroindolylethyl-sulphonamide according to claim 1 or a physiologically acceptable salt thereof and a pharmaceutically suitable excipient or solvent.

6. A method of treating thromboses, thromboembolisms and ischaemias comprising administering to a patient requiring such treatment an effective amount of an N-dihydroindolylethyl-sulphonamide according to claim 1 or a physiologically acceptable salt thereof.

7. A method of combating asthma or allergy comprising administering to a patient requiring such treatment an effective amount of an N-dihydroindolylethyl-sulphonamide according to claim 1 or a physiologically acceptable salt thereof.

* * * * *